United States Patent [19]
Bregen et al.

[11] Patent Number: 5,728,135
[45] Date of Patent: Mar. 17, 1998

[54] STIFFENED SUTURE FOR USE IN A SUTURING DEVICE

[75] Inventors: Michael Francis Bregen, Milford, N.J.; John Paul Measamer, Cincinnati, Ohio

[73] Assignee: Ethicon, Inc., Somerville, N.J.

[21] Appl. No.: 598,886

[22] Filed: Feb. 9, 1996

[51] Int. Cl.⁶ .................................................. A61B 17/04
[52] U.S. Cl. .................. 606/228; 606/232; 606/148; 606/139
[58] Field of Search ................................ 606/224, 232, 606/225, 226, 228, 230, 139, 148

[56] References Cited

U.S. PATENT DOCUMENTS

| | | | |
|---|---|---|---|
| 3,890,975 | 6/1975 | McGregor | 128/339 |
| 5,074,874 | 12/1991 | Yoon | 606/224 |
| 5,312,436 | 5/1994 | Coffey et al. | 606/228 |
| 5,383,901 | 1/1995 | McGregor et al. | 606/223 |
| 5,383,904 | 1/1995 | Totakura et al. | 606/228 |
| 5,425,746 | 6/1995 | Proto et al. | 606/224 |
| 5,454,834 | 10/1995 | Boebel et al. | 606/228 |
| 5,501,690 | 3/1996 | Measamer et al. | 606/146 |

FOREIGN PATENT DOCUMENTS

| | | | |
|---|---|---|---|
| 509 547 | 4/1992 | European Pat. Off. | A61L 17/00 |
| 93 13714A | 7/1993 | WIPO | A61B 17/04 |

*Primary Examiner*—Michael Buiz
*Assistant Examiner*—Tina T. D. Pham
*Attorney, Agent, or Firm*—Hai Brent Woodrow

[57] ABSTRACT

A suture for use in a laparoscopic suturing device comprising a suture having a first and second end. The first end being attached to a surgical needle and the second end being attached to a retainer wherein the adjacent to the retainer there is a stiffened segment of the suture.

15 Claims, 2 Drawing Sheets

STIFFENED SUTURE FOR USE IN A SUTURING DEVICE

FIELD OF INVENTION

This invention relates to an improved suture and more particularly, to a suture with a surgical needle on one end, a retainer attached to the other end and a stiffened segment of suture adjacent thereto.

BACKGROUND OF THE INVENTION

For surgeons, suturing has long been the standard method for tissue fastening and repair. But, with the advent of laparoscopic surgery, surgeons were removed from the immediacy of contact with the surgical site that facilitated suturing. The complicating aspects of laparoscopic suturing are the handling of the needle, the accurate placement of a stitch and the tying of a knot in the laparoscopic environment. The current techniques are complicated, take many hours to master, and are easily forgotten. As a result, many surgeons avoid laparoscopic suturing, preferring instead to either use alternative tissue fastening method (clips, staples, endo-loops or loop-sutures), or to avoid those laparoscopic procedures which could require suturing.

SUMMARY OF THE INVENTION

The invention describe herein is for use in a laparoscopic suturing device comprising a suture having a first end and a second end. The first end being attached to a surgical needle and the second end attached to a retainer wherein adjacent to said retainer is a stiffened segment of suture.

DETAILED DESCRIPTION OF THE INVENTION

Figure 1:
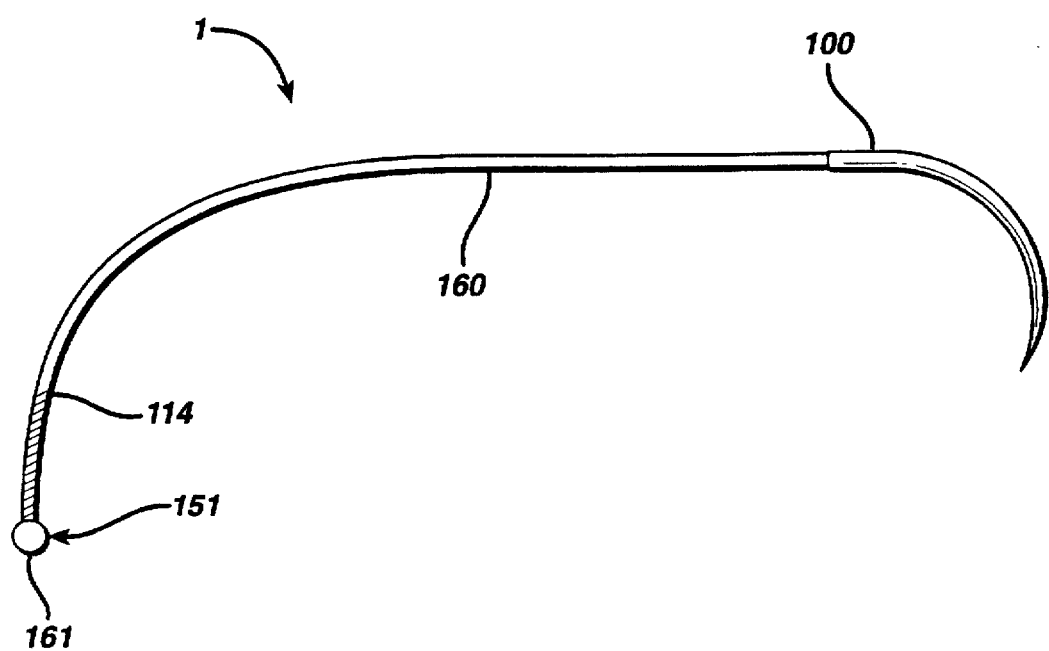
FIG. 1 is a perspective view of the stiffened suture with a needle attached to the suture on one end (armed). On the other end of the suture is a retainer adjacent to the retainer is a stiffened segment.
Figure 2:
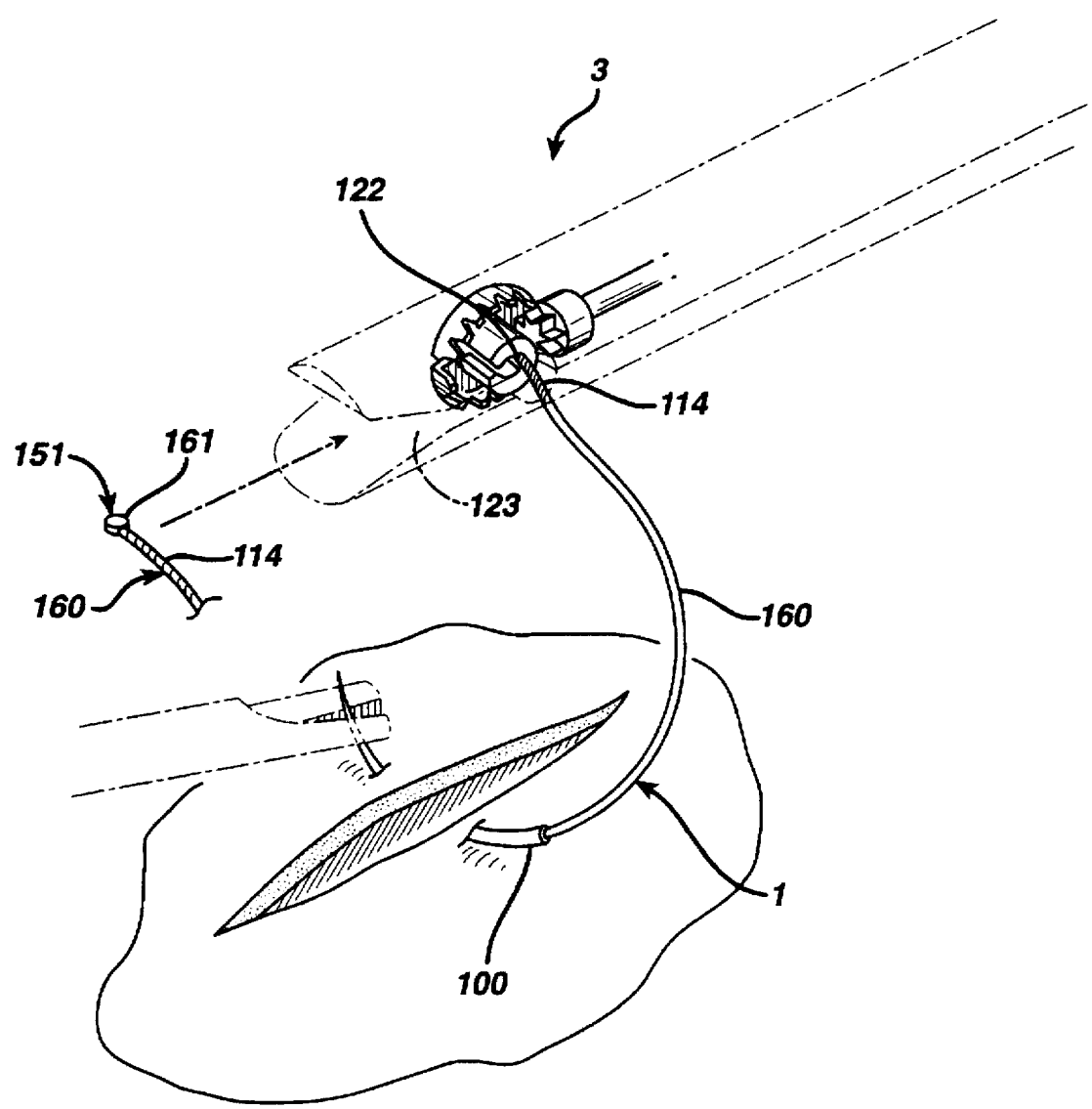
FIG. 2 is a perspective view of the armed stiffened suture loaded in a knot-tying mechanism.

Referring to FIG. 1 in which the preferred embodiment of the present invention is illustrated, the stiffened suture 1 is composed of a suture 160 having a first and second end. Attached to the first and for most surgical procedures is a surgical needle 100. Attached to the second end of the suture is a retainer 151 which in the preferred embodiment is a ferrule 161. The retainer could also be a knot or other device which increased the suture diameter so that it will not pass through passage 122 of the endoscopic suturing device 3 illustrated in FIG. 2. Adjacent to the retainer 151 toward the first end of the suture is a stiffened segment 114. The stiffened segment 114 should be in the range of from about ½ inch to about 3 inches in length and preferably 2 inches.

The stiffened segment 114 facilities the rapid reloading of new stiffened sutures into the endoscopic suturing device 3. The stiffened segment allows the surgeon to quickly place the stiffened segment 114 into the notch 123 of the endoscopic suturing device. A complete description of the endoscopic suturing device is provided in application Ser. No. 08/319,182, filed Oct. 6, 1994, entitled, "Needle Driving Device" by Measamer et al. (hereby incorporated by reference herein).

Suture 1 can be fabricated of either bioabsorbable polymeric resins or of non-bioabsorbable biocompatible materials. Suitable bioabsorbable polymeric resins include, for example, homopolymers and copolymers derived from monomers selected from the group consisting of glycolic acid, glycolide, lactide, lactic acid, 1,4-dioxepan-2-one, p-dioxanone, ε-caprolactone, trimethylene carbonate and mixtures thereof. Polymers and copolymers of the foregoing kind and absorbable surgical devices made therefrom are well known.

Examples of suitable non-bioabsorbable biocompatible materials include homopolymers and copolymers of polypropylenes, silks, polyamides, polyesters, polyvinyl chlorides, polytetrafluoroethylenes and polysulfones. Materials of the foregoing kind are well known. The suture may include suitable dyes, coatings, plasticizers, fillers, etc., as desired or appropriate to improve the visibility and/or handling characteristics of the suture. The stiffening agent preferably is applied after the coated or dyed suture is attached to the retainer.

Suitable stiffening agents are biocompatible materials capable of stiffening the suture sufficiently to allow the quick insertion of the stiffened suture and eyelet (or knot) into the suturing device. Such stiffening agents are preferably liquids, soluble in common solvents, or low melting solids for ease of application to the suture and may be either bioabsorbable or non-bioabsorbable. Examples of such stiffening agents include homopolymers and copolymers of epoxies, vinyl alcohols, hydroxy alkyl methacrylates, acrylamides, n-vinyl pyrrolidones, alkylene oxides, cyanoacrylates, low melting polylactone polymers and copolymers (melting at less than about 100° C.) and mixtures thereof. Other suitable stiffening agents include waxes, shellacs, carboxyalkyl celluloses, alginic acid, poly-n-acetyl glucose amines, gelatins, collagens, hyaluronic acids and mixtures and copolymers thereof. These stiffening agents may be water soluble. Stiffening agents should have no appreciable toxicity to the body when present at the levels present sufficient to obtain the desired degree of stiffening.

To be suitable, for applying a stiffening agent to the suture, a solvent must (1) be miscible with the stiffening agent at a suitable concentration of stiffening agent, (2) have a sufficiently high vapor pressure to be readily removed by evaporation, (3) not appreciably affect the integrity of the retainer and/or suture and (4) capable, in combination with the stiffening agent, of wetting the surface of the suture.

Application of the stiffening agent to the suture can be carried out in any number of ways. Thus, for example, the region of the suture adjacent to the ferrule can be submerged in the stiffening agent, or solution thereof, until a suitable quantity of stiffening agent sufficient to obtain the desired stiffening is acquired or otherwise retained by the sutures after removal of any excess agent and/or accompanying solvent, if any. The excess stiffening agent or solvent may be removed by drainage, wiping, evaporation, etc. In many cases, contact times on the order of from just a few seconds, e.g. about 2 to about 50 seconds to several minutes or hours, e.g. about 2 to about 50 minutes or about 1 to about 2 hours and even longer, as long as the contact time is sufficient to impart an amount of stiffening agent to the suture to provide the desired degree of stiffness to the stiffened segment of the suture, as compared with the same type of surgical article which has not been treated with the stiffening agent. Preferably the stiffness of the stiffened segment will be in the range of 0.2 to 1.0 kgf.cm$^2$ as measured on a Kawabata Bending Rigidity Tester.

Alternatively, the stiffening agent and solutions thereof can be applied by coating, spraying, brushing, etc., on the surfaces of the surgical device such that the latter receives and retains a sufficient quantity of the stiffening agent to decrease the probability of tangling or twisting thereof. It may be advantageous to perform one or more applications of the stiffening agent where particular functional properties are desired.

The surgical devices of the present invention are generally useful in endoscopic suturing devices for the closing of wounds of living tissue therewith.

We claim:

1. A method for rapidly reloading an endoscopic suturing device comprising inserting into an endoscopic suturing device having a passage a stiffened segment of a surgical device suturing device comprising a a first and second end, the first end being attached to a needle and the second end being attached to a retainer, adjacent to the retainer is a stiffened segment of the suture wherein the retainer is adapted to not pass through a passage of the endoscopic suturing device.

2. The method of claim 1 wherein the stiffened segment is in the range of from about ½ to about 3 inches in length.

3. The method of claim 1 wherein the suture is a multifilament suture.

4. The method of claim 1 wherein the retainer is a ferrule.

5. The method of claim 1 wherein the suture is bioabsorbable.

6. The method of claim 1 wherein the suture is made from a polymer composed of monomers selected from the group consisting of glycolic acid, glycolide, lactide, lactic acid, 1,4-dioxepan-2-one, p-dioxanone, ε-caprolactone, trimethylene carbonate and mixtures thereof.

7. The method of claim 1 wherein the stiffened segment is formed by applying a stiffening agent which is a polymer selected from the group consisting of epoxies, vinyl alcohols, hydroxy alkyl methacrylates, acrylamides, n-vinyl pyrrolidones, alkylene oxide, cyanoacrylates, low melting polylactone polymers and low melting polylactone copolymers and mixtures thereof.

8. The method of claim 1 wherein the stiffened segment is formed by applying a stiffening agent selected from the group consisting of waxes, shellacs, carboxyalkyl celluloses, alginic acid, poly-n-acetyl glucose amines, gelatins, collagens, hyaluronic acids and mixtures thereof.

9. The method of claim 1 wherein the suture is a nonbioabsorbable polymers selected from the group consisting of polypropylenes, silks, polyamides, polyesters, polyvinyl chlorides, polytetrafluoroethylenes and polysulfones.

10. A kit comprising a an endoscopic knot tying device having a passage and a device composed of a suture having a first and second end, the first end being attached to a needle and the second end being attached to a retainer adapted to not pass through the passage, adjacent to the retainer is a stiffened segment of the suture suitable for use in the suturing device.

11. The kit of claim 10 wherein the stiffened segment is in the range of from about ½ to about 3 inches in length.

12. The kit of claim 10 wherein the suture is a multifilament suture.

13. The kit of claim 10 wherein the retainer is a ferrule.

14. The kit of claim 10 wherein the suture is bioabsorbable.

15. The kit of claim 10 wherein the suture is non-bioabsorbable.

* * * * *